United States Patent
Zeng et al.

(10) Patent No.: US 10,323,922 B2
(45) Date of Patent: Jun. 18, 2019

(54) LOCALIZATION AND TRACKING OF AN OBJECT

(71) Applicant: CARDIOINSIGHT TECHNOLOGIES, INC., Cleveland, OH (US)

(72) Inventors: Qingguo Zeng, Solon, OH (US); Ping Jia, Solon, OH (US); Charulatha Ramanathan, Solon, OH (US); Lijun Yu, Cleveland, OH (US); Jeff Burrell, Euclid, OH (US); Brian George, Medina, OH (US); Qing Lou, Powell, OH (US); Ryan Bokan, Cleveland, OH (US); Soniya Bhojwani, Cleveland, OH (US)

(73) Assignee: CARDIOINSIGHT TECHNOLOGIES, INC., Cleveland, OH (US)

( * ) Notice: Subject to any disclaimer, the term of this patent is extended or adjusted under 35 U.S.C. 154(b) by 924 days.

(21) Appl. No.: 14/841,198

(22) Filed: Aug. 31, 2015

(65) Prior Publication Data
US 2016/0061599 A1 Mar. 3, 2016

Related U.S. Application Data

(60) Provisional application No. 62/043,565, filed on Aug. 29, 2014.

(51) Int. Cl.
*G01B 7/00* (2006.01)
*A61B 5/08* (2006.01)
(Continued)

(52) U.S. Cl.
CPC .............. *G01B 7/003* (2013.01); *A61B 5/061* (2013.01); *A61B 19/5244* (2013.01); *A61B 2019/5246* (2013.01)

(58) Field of Classification Search
CPC ................................. G01B 7/003; A61B 5/061
See application file for complete search history.

(56) References Cited

U.S. PATENT DOCUMENTS 4,949,725 A      8/1990   Raviv et al.
5,697,377 A  *  12/1997   Wittkampf ............. A61B 5/042
                                                              128/899
(Continued)

FOREIGN PATENT DOCUMENTS

EP        1181891         9/2003
EP        2064987 A1      6/2009
(Continued)

OTHER PUBLICATIONS

Wikipedia: Electric Dipole Moment https://web.archive.org/web/20130429120916/https://en.wikipedia.org/wiki/Electric_dipole_moment, retrieved by archive.org on Apr. 29, 2013.*
(Continued)

*Primary Examiner* — Paul D Lee
*Assistant Examiner* — Mark I Crohn
(74) *Attorney, Agent, or Firm* — Tarolli, Sundheim, Covell & Tummino LLP

(57) ABSTRACT

This disclosure relates to localization and tracking of an object. As one example, measurement data can be stored in memory to represent measured electrical signals at each of a plurality of known measurement locations in a given coordinate system in response to an applied signal at an unknown location in the given coordinate system. A dipole model cost function has parameters representing a dipole location and moment corresponding to the applied signal. A boundary condition can be imposed on the dipole model cost function. The unknown location in the given coordinate system, corresponding to the dipole location, can then be determined based on the stored measurement data and the (Continued)

dipole model cost function with the boundary condition imposed thereon.

28 Claims, 6 Drawing Sheets

(51) Int. Cl.
*A61B 19/00* (2006.01)
*A61B 5/06* (2006.01)

(56) References Cited

U.S. PATENT DOCUMENTS

| | | | |
|---|---|---|---|
| 6,073,040 | A | 6/2000 | Kiyuna |
| 6,308,093 | B1 | 10/2001 | Armoundas et al. |
| 6,370,412 | B1 | 4/2002 | Armoundas et al. |
| 6,856,830 | B2 | 2/2005 | He |
| 7,020,512 | B2 | 3/2006 | Ritter et al. |
| 7,792,563 | B2 | 9/2010 | Cohen et al. |
| 8,032,209 | B2 | 10/2011 | He et al. |
| 2004/0230112 | A1 | 11/2004 | Scholz |
| 2006/0251303 | A1* | 11/2006 | He ............... A61B 5/04008 382/128 |
| 2009/0232220 | A1 | 9/2009 | Neff et al. |
| 2009/0245422 | A1 | 10/2009 | Sampath et al. |
| 2012/0197111 | A1 | 8/2012 | Bar-Tal |
| 2012/0253161 | A1 | 10/2012 | Harlev et al. |
| 2013/0079622 | A1 | 3/2013 | Wu et al. |
| 2013/0109996 | A1 | 5/2013 | Turnbull et al. |
| 2013/0243074 | A1 | 9/2013 | Bai |
| 2013/0317334 | A1* | 11/2013 | Bar-Tal ............... A61B 5/6852 600/373 |
| 2014/0105325 | A1 | 4/2014 | Huang et al. |
| 2014/0221803 | A1 | 8/2014 | Bar-Tal et al. |

FOREIGN PATENT DOCUMENTS

| | | | |
|---|---|---|---|
| EP | 1757227 A2 | 3/2012 | |
| EP | 2684519 A1 * | 1/2014 | ............ A61B 5/062 |
| WO | 199502995 A1 | 2/1995 | |
| WO | 2001/0025822 A1 | 4/2001 | |
| WO | 2008117981 | 10/2008 | |

OTHER PUBLICATIONS

Supplementary European Patent Application No. 15835344.2; Applicant: Cardiolnsight Technologies, Inc.; European Search Report; Examiner: Andrei Malcoci; Date of Completion: Jan. 31, 2018; 7 pgs.

PCT International Search Report and PCT Written Opinion of the Inernational Searching Uthority; International Application No. PCT/US2015/047785, Filing Date: Aug. 31, 2015; Date of Completion: Dec. 10, 2015; Authorized Officer: Ja Young Kim; 10 pgs.

"PCT International Search Report and PCT Written Opinion of the International Searching Authority"; PCT International Application No. PCT/US2015/049379; International Filing Date: Sep. 10, 2015; Authorized Officer: Do Weon Kim; Date of Completion: Dec. 23, 2015; 12.

* cited by examiner

LOCALIZATION AND TRACKING OF AN OBJECT

CROSS-REFERENCE TO RELATED APPLICATION

This application claims the benefit of U.S. provisional patent application No. 62/043,565 filed on Aug. 29, 2014 and entitled LOCALIZATION AND TRACKING OF AN OBJECT, which is incorporated herein by reference in its entirety.

TECHNICAL FIELD

This disclosure relates to localization and tracking of an object.

BACKGROUND

This section provides background information related to the present disclosure and is not necessarily prior art.

A navigation system can locate an object within a volume. For example, a navigation system can be used to track an instrument during a procedure, such as a surgical procedure. Various systems can be used to track instruments including electromagnetic systems, optical systems, magnetic systems acoustic systems, and the like. On particular approach is to localize an electrical source using a single equivalent dipole model. However, existing techniques tend to be insufficiently accurate or are incapable of real-time applications.

SUMMARY

This disclosure relates to localization and tracking of an object.

As one example, a method includes storing measurement data in memory to represent measured electrical signals at each of a plurality of known measurement locations in a given coordinate system in response to an applied signal at an unknown location in the given coordinate system. A dipole model cost function is provided with parameters representing a dipole location and moment corresponding to the applied signal. The method also includes imposing boundary condition on the dipole model cost function. The method also includes determining the unknown location in the given coordinate system, corresponding to the dipole location, based on the stored measurement data and the dipole model cost function with the boundary condition imposed thereon.

As another example, a method includes storing measurement data in memory representing measured electrical signals at each of a plurality of known locations in a given coordinate system in response to an applied signal at an unknown location residing in the given coordinate system. A dipole model cost function is provided having unknown parameters representing a dipole location and moment as a function of the measured electrical signals. The dipole model cost function also parameterizes noise associated with the measured signals. The method also includes determining the unknown location in the given coordinate system, corresponding to the dipole location, based on the dipole model and the stored measurement data.

As yet another example, a system includes memory that stores geometry representing a plurality of measurement locations around a volume and anatomical data registered in a given coordinate system. A measurement system receives signals measured at the plurality of measurement locations, including in response to a signal applied to a location within the volume, and provides measurement data representing the measured signals at each of the plurality of measurement locations. The measurement data is stored in the memory. A localization system includes a dipole model cost function having unknown parameters representing a dipole location and moment, corresponding to the applied signal. The localization system imposes a boundary condition on the dipole model cost function to determine the location of the applied signal in the given coordinate system, corresponding to the dipole location, based on the measurement data.

DETAILED DESCRIPTION

This disclosure relates to localization and tracking of an object. The approach can be implemented to noninvasively and in real-time, locating and tracking the position of an electric signal emitting object, such as a catheter or other probe. As disclosed herein, a dipole model can be applied to compute an estimate of a dipole location and moment in a three-dimensional coordinate system based on a plurality of measurements obtained concurrently at known locations. In some examples, a boundary condition can be applied to constrain an optimization that is implemented to compute the location and moment of the dipole. As one example, the boundary condition can be applied as part of preprocessing prior to computing the optimization for dipole localization. As another example, the boundary condition can be integrated into the formulation optimization itself. Additionally or alternatively, the dipole model can be configured to account for noise in the measurements of electrical signals utilized in the dipole localization. The measurements for the electrical signals can be non-invasive measurements, invasive measurements or a combination of invasive and non-invasive measurements.

The location and moment for the dipole can be further employed to display graphically an indication of position for the signal emitting object, such as can correspond to one or more electrodes on a catheter or other probe. A collection of location information can be collectively displayed to represent a surface or incorporated in a graphical map of patient anatomy or generic model by co-registering the determined location coordinates with anatomical geometry (e.g., for a given patient or a generic model).

Figure 1:
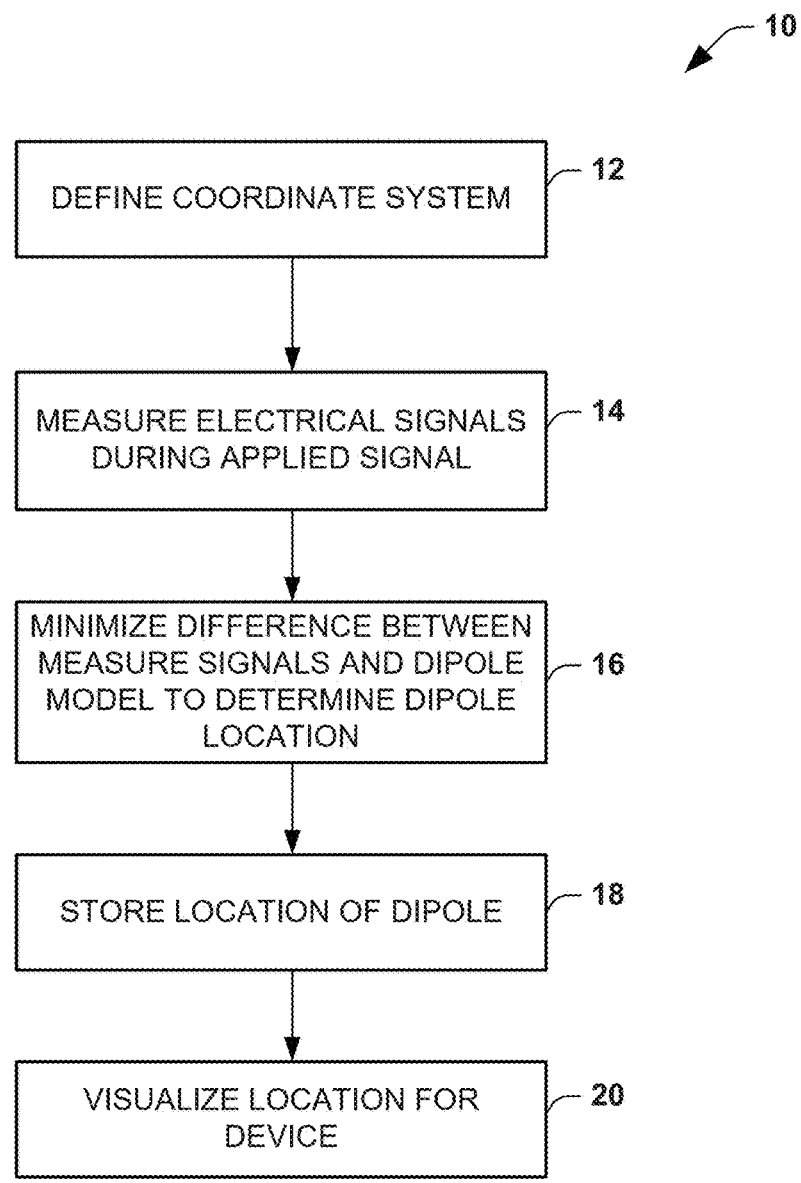
FIG. 1 is a flow diagram depicting an example of a method for performing localization of a dipole.

FIG. 1 demonstrates an example of a localization method 10. The method 10 can be used to localize an electrical field source within a patient's body based upon sensed electrical measurements at each of a plurality of known spatial locations. The field source can include one or more artificially applied fields, such as from an electrode on a fixed or moveable device. In other examples the field source can correspond to biological signals, such as HIS bundle during QRS complex or pacing signals. Each such source can be represented a dipole model, having a dipole location and moment (direction and magnitude). The dipole model(s) can be adapted, via an optimization function, to determine the location of the field source based on measured electrical signals acquired in a non-invasive, invasive or hybrid non-invasive and invasive manner.

The method begins at 12 to define a spatial coordinate system. The coordinate system, for example, is a three-dimensional coordinate system that has been registered with respect to a patient's anatomy. The coordinate system can be derived from processing image data that includes sensors spatial locations as well as patient anatomy, as disclosed herein. The measurement system can include an arrangement of sensors (e.g., electrodes) distributed over a portion of the patient's torso surrounding the region in which the localization is to be performed. The locations of the sensors during localization can be the same or having a known spatial relationship with respect to the sensor locations in the image data used to define the coordinate system.

At 14, electrical signals are measured. The electrical signals are measured during a time that includes application of a localization signal. The localization signal can be a predetermined or otherwise deterministic signal that is applied at a site within a volume (e.g., patient's body) at an unknown location, which corresponds to the source being localized. The applied signals for dipole based localization can be any electrical signal including but not limited to pacing signals, or sinusoidal or square waves delivered to bipolar lead pairs from catheter.

There can be more than one such source that can apply respective signals. When more than one signal is applied at different sites being localized during the method 10, the signals can be differentiated. For instance, to detect multiple dipoles using pacing signals, the different lead pairs can be can be energized at different time instances to differentiate the signals corresponding to the different lead locations. To detect multiple dipoles using sinusoidal or square waves, such signals can be applied at different identifiable times (e.g., identified time stamps), concurrently at different frequencies or having other signal characteristics that can be identified individually. The measured electrical signals can be stored in memory as measurement data representing measured electrical signals at each of a plurality of known locations (e.g., measured by sensors at locations determined a priori) with respect to the given coordinate system (at 12).

As one example, the measurements can be from sensors located non-invasively on a patient's body and the locations of such sensors in the given coordinate system can be known (as in body surface potential mapping). For instance, the sensor locations can be determined in the desired coordinate system based on image data from an imaging modality, based on using a digitizer and/or other measurements. For instance, the measurement data is based on a distributed arrangement of multiple sensors (e.g., about 250 or more sensors) positioned completely around the region where the unknown location resides, such as can be mounted to a wearable garment (e.g., vest) in which each of the electrodes has a known location in the given coordinate system. For example, the sensor array can be implemented as a non-invasive type of sensor apparatus as disclosed in U.S. Patent Publication No. 2013/0281814, entitled Multi-Layered Sensor Apparatus; although other configurations of sensor apparatuses could be utilized. As another example, measurements used for the dipole localization can be located in the body or a hybrid approach that employs both invasive and non-invasive sensors can be used.

The applied signal can be generated from one or more electrodes located at a position that is unknown and to be determined by the localization approach herein. One or more electrodes can be disposed on a probe, such as a catheter or other device, at predetermined locations relative to each other. A signal generator can apply a specific signal that can be measured and localized by applying the dipole model for each electrode as disclosed herein. For example, the applied signal can be a predetermined waveform that is distinguishable from anatomical generated signals, such as may be a pulse, a sinusoidal waveform or the like that can be generated by a signal source electrically connected to the electrode(s) being localized. Extraneous signals (e.g., electrograms, noise or other signals) can be filtered out of the measurements, for example.

In some examples, a proper subset of measurements from each of the plurality of sensors can be selected for computing the dipole position. For example, channels for sensors determined to be noisy (e.g., based on SNR) or otherwise inadequate (e.g., based on body surface measurements) can be excluded from use in the dipole position calculation. If a given sensor excluded, neighboring sensor measurements (e.g., from a set of adjacent sensors surrounding the excluded sensor) can be interpolated to compute a virtual sensor measurements for use in computing the dipole location or, alternatively, the excluded channel(s) can be omitted altogether from such dipole computation.

At 16, the method 10 includes determining a dipole location and moment according to a predetermined optimization function for the dipole model. That is, the electrical signals measured at 14 provide known values that are used in the optimization function to find extrema that define the location and moment of the dipole with respect to the given coordinate system. As disclosed herein, the localization method 10 employs a dipole model cost function having parameters (variables) representing a dipole location and moment for localizing the source of the applied signal. The dipole location thus can be calculated as an optimization problem that fits the dipole model cost function to the data represented the measured electrical signals at each of the sensor locations, which are known in the coordinate system (at 12). In some examples, the determination at 16 can implement a boundary condition, as disclosed herein. Additionally or alternatively, the dipole model cost function can consider noise that exists in the electrode measurements (at 14).

At 18, the determined location and moment of the dipole can be stored in memory. The memory can include any local or remote memory (e.g., volatile and/or non-volatile memory) that is accessible for retrieval, such as for use by the same or different computer. The dipole location that is stored can thus represent spatial coordinates for the localized source. As mentioned, in some examples, there are multiple sources, which may be on the same or different probe, and respective locations can be stored at 18 for each such source. At 20, the location for the source is visualized, such as in a display, printed output or the like. For example, the identified location can be overlaid in a graphical map of a patient's anatomy, such as a heart or other anatomic region where the source was localized to reside via the method. By determining the dipole location and graphical map in a common coordinate system or (via registration or transform) visualization of the dipole location, as well as a device carrying the field source for which the dipole location was determined at 16, is facilitated.

In the three dimensional coordinate system (defined at 12), the unknown parameters of the dipole model cost function determined at 16 can include the spatial coordinates for the 3D position of the dipole (r') and the dipole moment (p, having magnitude and direction). These unknown parameters can be computed as a function of the measurements and known spatial locations for such measurements. Additionally, since the dipole moment can be expressed in terms of the dipole location, as disclosed herein, the mathematical functions for the model can be expressed in terms of the unknown dipole location. Thus, the dipole model can parameterize the moving dipole as a vector having a dipole location parameter and a dipole moment parameter with respect to the given coordinate system.

The following examples provide a further basis that can be employed to determine dipole location r'. These examples are applicable to the method 10 of FIG. 1 as well as in other methods and systems disclosed herein.

As an example, a general Equivalent Single Dipole (ESD) representation of a potential $\phi$ generated by a single dipole in an infinite homogeneous medium can be represented as follows:

$$\phi(r, r', p) = \frac{1}{4\pi g} \frac{p \cdot (r - r')}{|r - r'|^3} \quad (1)$$

where g is the conductivity, p is the dipole moment, r' is the dipole location, and r is the location of an observation point.

The position and orientation of an electrical signal provided from a signal-emitting object can be ascertained based on the dipole components (direction, magnitude) of p and location r', given electrical potential measurements $\phi_m^i$ collected at known electrode locations r', where i=1, ..., N. As one example, an optimization function for the dipole model in (1) can be implemented by minimizing a least squares cost function representing a difference based on the measured electrical signals and a dipole field computed for the dipole model over a set of locations residing in the given coordinate system. Such example of dipole model cost function can be expressed in the form of a least square fitting model as follows:

$$\min_{p, r'} E(p, r') := \quad (2)$$

$$\min_{p, r'} \sum_{i=1}^{N} \|\phi_m^i - \phi^i(p, r')\|^2 = \min_{p, r'} \sum_{i=1}^{N} \left\| \phi_m^i - \frac{1}{4\pi g_i} \frac{p \cdot (r^i - r')}{|r^i - r'|^3} \right\|^2$$

In another example, the dipole model can be expanded to consider noise in the measurements $\phi_m^i$. For instance, to identify dipole components (direction, magnitude) of p and location r', given measurements $\phi_m^i$ collected at locations r' for each of the sensors, considering noise in measurements, another example is to consider the difference $\phi_m^i - \phi^i$ as independent normal random variables with variance $\sigma$ indexed by the location $r^i$ with probability density functions, such as follows:

$$p(\phi_m^i - \phi^i) = \frac{1}{\sqrt{2\pi}\,\sigma} e^{-\frac{|\phi_m^i - \phi^i|^2}{2\sigma^2}} \quad (3)$$

To identify the dipole components, one the log-likelihood function can be maximized in an optimization function, such as by minimizing a negative log-likelihood model cost function with respect to the dipole location and moment. The optimization function, for example, can be solved by numerical methods to identify optimal components and variance by minimizing the following function with respect to dipole moment p and location r'. An example expression for such log-likelihood function can be expressed as follows:

$$\min_{p, r'} E(p, r') := \min_{p, r'} \left[ -\sum_{i=1}^{N} \ln(p(\phi_m^i - \phi^i(p, r'))) \right] := \quad (4)$$

$$\min_{p, r'} \sum_{i=1}^{N} \left( \frac{|\phi_m^i - \phi^i(p, r')|^2}{2\sigma^2} + \ln(\sqrt{2\pi}\,\sigma) \right)$$

For given measurements $\phi_m^i$, if the variance $\sigma$ of the difference can be pre-calculated, then the model in (4) is equivalent with the least square approach. For instance, the variance can be computed in advance of localization (e.g., during a calibration phase) and stored in memory to facilitate subsequent calculations (e.g., at 16 of FIG. 1).

The example cost function in (4) assumes a constant variance for the noise measurements. As another example, the noise variance can be allowed to vary, spatially across the measurements i ($\sigma_i$). For example, a value of $\sigma_i$ can be computed for each i, where each i can correspond to each respective sensor where measurements are made at known locations or to a spatial region including one or more sensors. Thus, similar to as in (4), but not assuming same variance across the board, namely the following assumption can be made:

$$\frac{\phi_m^i - \phi^i}{\sigma} \mathrel{\ddot{u}d} N(0, 1) \quad (5)$$

By minimizing the negative log-likelihood, dipole model cost function can be expressed as follows:

$$\min_{p, r'} E(p, r') := \quad (6)$$

$$\min_{p, r'} \left[ -\sum_{i=1}^{N} \ln\left( p\left( \frac{\phi_m^i - \phi^i(p, r')}{\sigma^i} \right) \right) \right] := \min_{p, r'} \sum_{i=1}^{N} \frac{|\phi_m^i - \phi^i(p, r')|^2}{2(\sigma^i)^2}$$

For a given optimization cost function for the dipole model (e.g., a least squares function or a log-likelihood function), various numerical methods can be implemented to calculate the dipole location and moment based on the electrical signals measured at 14. The numerical methods can include a brute-force search method or an iterative method (e.g., Newton's method, gradient descent methods, conjugate gradient method or the like), the simplex search method, or the Gauss-Newton method to name a few.

In each of the examples above (e.g., dipole model cost functions presented in (2), (4) and (6)), the respective cost function can be seeded with an initial location in the given coordinate system facilitate the determination of the coordinates for the dipole location. For instance, the initial location can be based on a previously determined unknown dipole location in the given coordinate system. Alternatively, a location within a region of interest can be use to seed the cost function to facilitate the minimization.

In some examples, each of the measured electrical signals is determined as a difference between the signal at each of the plurality of known locations with respect to a reference signal at a predefined location. For instance, the dipole model can be configured to represent the potential of the dipole with respect to the reference signal. The predefined reference location can be selected from one of the plurality of known sensor locations or another known location (e.g., Wilson Central Terminal (WCT)). For example, the predefined reference location is chosen regionally for each of the measured electrical signals according to the known location of the measured electrical signals to help compensate for effects of inhomogeneity through the body. Thus, all the formulations disclosed herein (above and below) can implemented using corrected versions of the measured signals $\phi_m^i$, instead of the direct measurements from each of the sensors.

As WCT is usually generated by taking average of electrode measurements from three specific locations, the drawback of WCT is that its location and signal are subjected to change based on different selection of the electrodes used in the average process, given the fact that the exact physical location of WCT is not known. To reduce the error due to different references used for ground, instead of modeling on the measurements directly, the difference of measurements can be modeled accordingly. For example, an electrode $r_{ref}$ at a known location can be selected from the array of electrodes, then the measurement difference between each location r and $r_{ref}$ can be integrated into the dipole model. For the example dipole model utilized in (2), using the corrected measurement difference, can expressed as follows:

$$(\phi_m^i - \phi_m^{ref}) - \left(\frac{1}{4\pi g} \frac{p \cdot (r^i - r')}{|r^i - r'|^3} - \frac{1}{4\pi g} \frac{p \cdot (r^{ref} - r')}{|r^{ref} - r'|^3}\right) \to 0 \quad (7)$$

With the reference correction being applied for each of the i measurements, $\phi_m^i$, the example least square fitting in (2) can be rewritten to following example formulation:

$$\min_{p,r'} E(p, r') := \min_{p,r'} \sum_{i=1}^{N} \|(\phi_m^i - \phi_m^{ref}) - (\phi^i(p, r') - \phi^{ref}(p, r'))\|^2 \quad (8)$$

$$= \min_{p,r'} \sum_{i=1}^{N} \left\|(\phi_m^i - \phi_m^{ref}) - \left(\frac{1}{4\pi g_i} \frac{p \cdot (r^i - r')}{|r^i - r'|^3} - \frac{1}{4\pi g_{ref}} \frac{p \cdot (r^{ref} - r')}{|r^{ref} - r'|^3}\right)\right\|^2$$

In the examples mentioned above, the conductivity has been considered as a constant for sake of simplicity. By way of further example, the example dipole model cost functions further can be modified to consider non-uniform conductivity for the body medium. While for electrodes in close neighborhood, conductivity shall be close. Therefore, the electrodes can be grouped into respective subsets based on regions $S_k$, k=1 ... K. Such groupings result in the following minimization formulation for the least square fitting example in (2):

$$\min_{p,r'} E(p, r') := \min_{p,r'} \sum_{k=1}^{K} \sum_{\substack{i=1 \\ r^i, r^{ref_k} \in S_k}}^{N_k} \|(\phi_m^i - \phi_m^{ref_k}) - (\phi^i(p, r') - \phi^{ref_k}(p, r'))\|^2 \quad (9)$$

$$= \min_{p,r'} \sum_{k=1}^{K} \sum_{\substack{i=1 \\ r^i, r^{ref_k} \in S_k}}^{N_k} \left\|(\phi_m^i - \phi_m^{ref_k}) - \left(\frac{1}{4\pi g} \frac{p \cdot (r^i - r')}{|r^i - r'|^3} - \frac{1}{4\pi g} \frac{p \cdot (r^{ref_k} - r')}{|r^{ref_k} - r'|^3}\right)\right\|^2$$

These reference points $r^{ref_k}$ can be a point with good signal quality in the region $S^k$, or some location close to the centroid of the region $S^k$. By using different regions, the impact due to non-uniform conductivity can be reduced.

Instead of using fixed reference points for each region, one can also use combinatorial pairs for each region, in the following example formulation:

$$\min_{p,r'} E(p, r') := \min_{p,r'} \sum_{k=1}^{K} \sum_{\substack{(i,j) \\ r^i, r^j \in S_k}} \|(\phi_m^i - \phi_m^j) - (\phi^i(p, r') - \phi^j(p, r'))\|^2 \quad (10)$$

$$= \min_{p,r'} \sum_{k=1}^{K} \sum_{\substack{(i,j) \\ r^i, r^j \in S_k}} \left\|(\phi_m^i - \phi_m^j) - \left(\frac{1}{4\pi g} \frac{p \cdot (r^i - r')}{|r^i - r'|^3} - \frac{1}{4\pi g} \frac{p \cdot (r^j - r')}{|r^j - r'|^3}\right)\right\|^2$$

As an alternative example to providing least square fitting as in (9) and (10) to consider non-uniform conductivity by employing corresponding reference and pairing electrodes, such concept is equally applicable to other dipole model cost functions. For example, the concept of using reference and pairing electrodes can be applied to dipole model cost functions, including the log-likelihood dipole model cost functions, such as by modifying (4) and (6) accordingly.

To help improve accuracy of the computed dipole location, the determination (e.g., at 16 in FIG. 1) can be constrained by imposing a boundary condition. In some examples, the boundary condition can be implemented by preprocessing applied to the signal measurements. Additionally or alternatively, a boundary condition can be integrated into the dipole model cost function.

Figure 2:
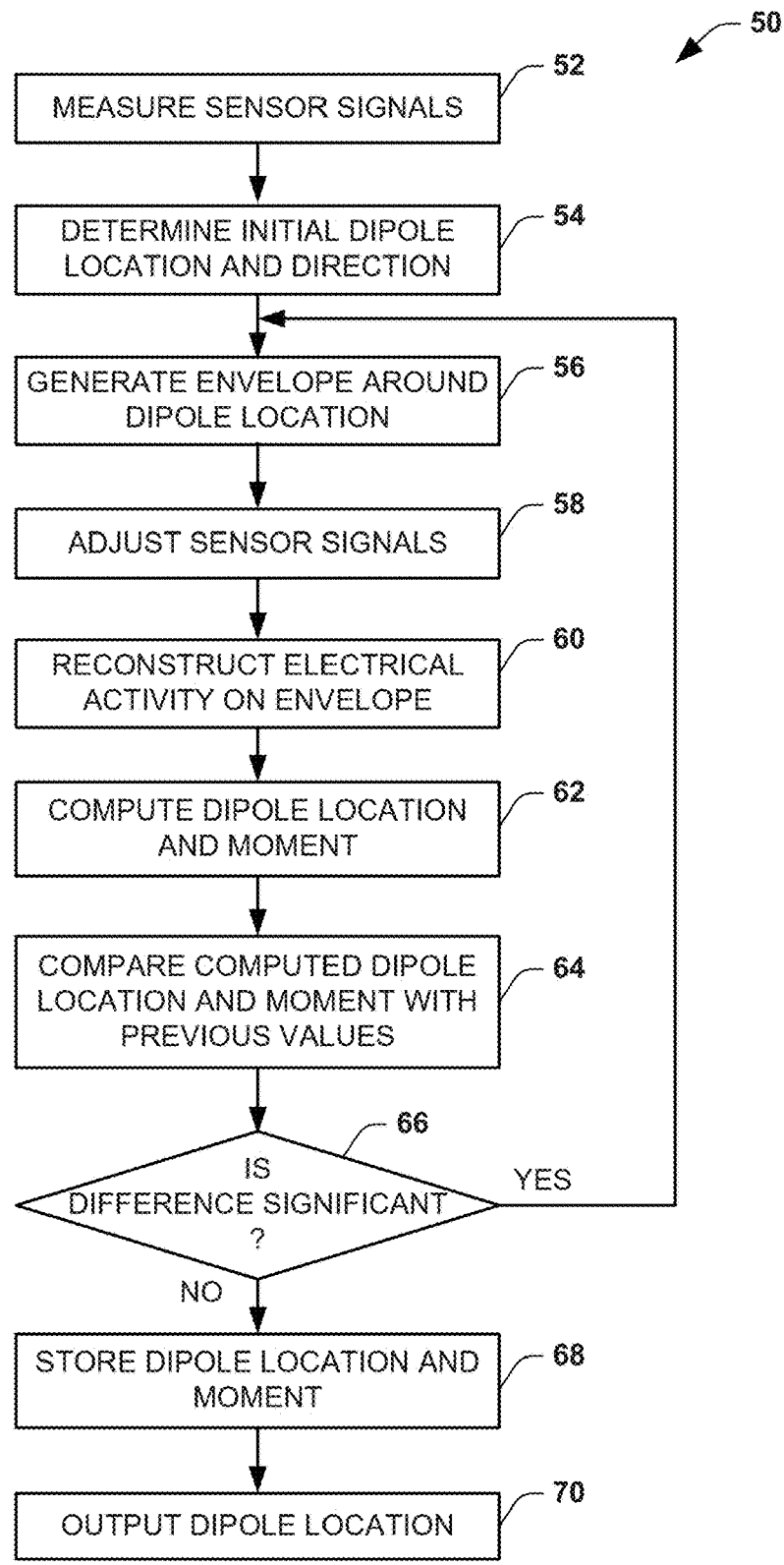
FIG. 2 is a flow diagram depicting an example of another method for performing localization using a boundary condition.

FIG. 2 depicts an example of another method 50 that can be utilized to localize a source of an applied signal corresponding to the method 10 of FIG. 1. In the example of FIG. 2, the fitting of the dipole model to the measured electrical signals is constrained by a boundary condition. Thus it is to be understood that the method of FIG. 2 can utilize the method of FIG. 1 in computing the dipole location in a manner that is constrained by a boundary condition. In the example of FIG. 2, the boundary condition is implemented by preprocessing electroanatomic data (e.g., electrical measurements and geometry data).

In the method of FIG. 2, at 52, sensor signals are measured at plurality of locations known with respect to a given three-dimensional coordinate system. For example, the known measurement locations can correspond to centroids of sensor electrodes positioned on the body surface, such as disclosed herein. In some examples, the measurements at 56 can be computed with respect to one or more selected reference points to refine the measurements of the electrical signals that are utilized for the localization, such as disclosed. For example, each of the measured electrical signals is determined as a difference between the signal at each of the plurality of known locations with respect to a reference measurement signal at a predefined one of the locations or another body surface location (e.g., a WCT), which may or may not be known in the coordinate system, and is separate and spaced apart from the array of sensors electrodes at the known locations. For instance, the dipole model can be configured to represent the potential of the dipole with respect to the reference signal. The predefined reference location can be selected from one of the plurality of known sensor locations or another known location.

At 54, an initial dipole location and moment are determined. The initial dipole location and moment can be computed using the method of FIG. 1 or other methods. For example, an initial estimate can be provided as a function of measured signals at the sensor locations, such as by minimizing the cost function in (2) or according to another model function. In other examples, an initial location can be set to a geometric center of the search domain, such as the center of the patient's heart as defined by the geometry data (e.g., derived from imaging data). In other examples, an initial dipole location and moment can be selected (e.g., randomly) within the search domain.

At 56, an envelope is generated around the dipole location which can be the initial dipole location determined at 54 or another updated location as disclosed herein. The envelope can correspond to any geometric construct that can be mathematically estimated within the search domain. As an example, the envelope can correspond to a sphere that defines a surface between the outer surface of the patient's body (where measurement electrodes reside) and the initial dipole location. While a sphere provides a geometry that will facilitate computations due to its rotational symmetry, other geometries can also be utilized, such as an ellipsoid, a cube or the like that surrounds the point that is to be localized according to the method 50. For instance, the envelope can be a cardiac envelope, such as corresponding to or including a portion of an epicardial surface of a patient's heart, an epicardial surface of model heart (the patient's or a generic heart) or to any surface boundary within the patient's body having a known spatial relationship with respect to the patient's heart or a model heart to which the object, represented by the dipole model, is being localized.

At 58, the signals measured at 52 are adjusted. The adjustments can include subtracting each of the measurements from a corresponding measurement at a selected reference sensor (e.g., a reference channel). Various approaches can be implemented to select the reference channel. For example, a plane can be defined as going through the dipole location (the initial at 54 or previously computed at 62) with such plane being normal to the dipole direction. The sensor location that is determined to be closest to the plane can be chosen as the reference channel. The measurements for each of the other channels can be subtracted measurement from this reference point to put the reference potential be 0 (e.g., ground). Additionally, the reference selection can take into account signal quality. For example, only channels with sufficient quality can be qualified for use as reference. Various quality metrics can be utilized to evaluate signal quality to define a set of channels from which the reference can be selected. Quality metrics can include SNR, standard deviation or the like. As another example, the reference selection can also be implemented by choosing a largest angle formed between the vector from dipole location to electrode location and vector of the dipole direction, or a similar approach for determining a geometric distance between sensor locations and the dipole location.

At 60, the adjusted signal measurements (from 58) are reconstructed onto the envelope (from 56). The inverse reconstruction onto the envelope can be implemented by solving the inverse problem. Examples of solutions to the inverse problem include the boundary element method (BEM) or the method of fundamental solution (MFS). For example, the reconstructed electrical activity on the envelope can be calculated with a boundary condition at the location where the sensors are located in the coordinate system (e.g., on the outside of the patient's body). Additional information relating to reconstructing electrograms onto the spatial envelope, which can be implemented at 60, is disclosed herein with respect to the electrogram reconstruction of FIG. 6.

At 62, the dipole location and moment are computed. The computation of the dipole location and moment at 62 can be implemented according to any of the methods disclosed herein (see, e.g., FIG. 1 and its corresponding description), for example. The computation at 62 utilizes the reconstructed electrical potentials on the envelope (computed at 60) as a boundary condition to calculate the new dipole location and moment. The dipole location and moment computations can be implemented numerically at 60 by applying a brute-force approach or other numerical method (e.g., a Gaussian method, simplex method or Gauss-Newton numerical method) to minimize a dipole model cost function. As disclosed herein, the dipole model cost function may be the least squares cost function for the dipole model as in (2) or another formulation. The dipole location that is determined at 62 can include a spatial point (or multiple points) that reside within a volumetric region of interest, such as a point within a spatial envelope associated with the heart in the patient's body (e.g., the envelope generated at 56). Alternatively or additionally, the dipole location can be computed to reside within or on a corresponding anatomical structure of the patient's body that has been co-registered with the coordinate system of the determined dipole location.

At 64, the dipole location and moment computed at 62 are compared relative to previously computed values of location and moment for the dipole. The previous values can correspond to the initial dipole location and moment from 54 (e.g., for a first loop of the method 50) or estimated values from a previous computation at 62. At 66, a determination is made as to whether there is a significant difference between the computed dipole location and moment and the previously computed values. The determination at 66 can compare the difference of the dipole vector (magnitude and direction) relative to a prescribed convergence threshold. If the difference does not exceed the threshold or is otherwise still considered significant at 66 (YES), the method returns to 56 to repeat 56 through 66.

With each loop of 56-66, the envelope is shifted based on newly identified dipole location (e.g., as computed at 62 in the previous loop). Also, in each loop of 56-66, the electrical activity (e.g., potentials) on the newly shifted envelop is recalculated solving the inverse problem (e.g., MFS or BEM). Thus, each loop employs an updated boundary condition, which is utilized to constrain the computation of the dipole location and moment at 62. The reference signal for adjusting the signal measurements at 58 can also be updated in each loop based on the location and moment of the dipole that was calculated in the preceding loop. The method thus will loop between 56 and 66 until the computed dipole location and moment correspond to the actual location and moment of the dipole of the source being localized according to the evaluation applied at 66. For instance, the significance threshold can be set to provide a desired level of accuracy (e.g., resolution) for estimating the dipole location. The localization method 50 will result in an absolute location of the source-emitting object based upon the electrical measurements of the applied signal from the object being localized.

Once the difference between the computed dipole location and moment does not exceed the threshold (NO), the method proceeds to 68 in which the dipole location and moment are stored in memory. The stored location thus can be output at 70, such as to be provided in a corresponding visualization as disclosed herein. The dipole moment (direction and magnitude) can also be provided in the output according to the computation at 60. As a result of calculating the dipole location and moment (at 62) for a given source positioned in the volume of interest (e.g., the patient's body), a graphical indication of the determined coordinates can be displayed. For example, the coordinates in space for the unknown location are mapped into three-dimensional geometry determined for anatomy (e.g., the patient's heart). A plurality of locations can be aggregated together to define a path or trajectory of a moving object. In another example, computed locations for the object contacting a surface within the patient's body can be aggregated together to define a corresponding surface geometry (e.g., an endocardial geometry) for one or more chambers or other anatomical or implanted objects with respect to known locations of the non-invasive sensors disposed on the patient's body surface.

For a given probe device (e.g., catheter) that includes a source be localized, the distance between bipolar leads is known. This distance prior information can be combined with computed dipole location and dipole moment, to enable reconstruction of the locations of the bipolar lead pair. For example, in addition to spacing between electrodes, the approach can also leverage the known electrode lengths and lead diameter to: (1) help reconstruct location of lead pair, and (2) optimize catheter visualization. One or more of these techniques can be applied for different bipolar pairs along one catheter to ascertain the overall layout of the catheter, or applied on different bipolar pairs across multiple catheters in the heart. For the example dipole approach, the bipolar leads do not need to contact with heart chambers.

As a further example, a boundary condition can be imposed on the localization method and in particular on the computation of the dipole location by integrating the boundary condition directly in the formulation of the dipole model cost function. In the context of using BEM for solving the inverse problem, for example, this can be referred to as a direct BEM method. The direct BEM approach will be described in reference to the dipole model shown in (2). However, each of the dipole models disclosed herein as well as other suitable models could likewise be formulated to impose similar boundary condition for dipole localization.

By way of example, given an electrical dipole within a closed surface T, with dipole location r and dipole moment p, then the electrical potential measurements $\phi_T(x)$ at spot x (e.g., electrode locations on the body surface) satisfies:

$$\phi_T(x) = \frac{1}{4\pi}\oint_{\partial T}\phi_T(s)\frac{\partial\left(\frac{1}{r}\right)}{\partial n}\cdot ds + \frac{p\cdot(r-x)}{4\pi\sigma|r-x|^3} \quad (11)$$

Using the boundary condition from 11, the dipole model cost function from Eq. 2 can be rewritten to include the boundary condition as a least squares minimization, such as follows:

$$\min\sum_i\frac{1}{2}\left(\phi_T(r^i) - \frac{1}{4\pi}\oint_{\partial T}\phi_T(s)\frac{\partial\left(\frac{1}{r}\right)}{\partial n}\cdot ds - \frac{p\cdot(r-r^i)}{4\pi\sigma|r-r^i|^3}\right)^2 \quad (12)$$

As disclosed herein, various mathematical model cost functions can be used to represent the dipole model as a mathematical optimization function in terms of its unknown parameters, namely dipole location and moment. For a given optimization function (e.g., a least squares function or a log-likelihood function) for the dipole model, various numerical methods can be implemented, individually or collectively, to calculate the dipole location and moment based on the electrical signals measured. The main numerical methods for solving the dipole model cost function can be categorized as brute-force search methods or iterative methods. Examples of some iterative approaches include gradient based approaches (e.g., Newton's method, gradient descent methods, conjugate gradient method or the like), the simplex search method, or the Gauss-Newton method to name a few.

By way of example, variable reduction can be utilized to simplify computations. In dipole formulations above, measurement is linear with respect to dipole moment p. For an optimal solution in any of the three formulations above, one can take express p in terms of location, r', by solving the following linear system:

$$\frac{\partial E(p,r')}{\partial p_i} = 0, i = 1, 2, 3 \quad (13)$$

Then all cost functions above can be treated as functions with respect to only r'.

The brute-force approach can be implemented with respect to each of the dipole model cost functions. For example, the candidate domain (envelop of the heart, atrial or ventricle or both) is partitioned into small regions, then the cost function is evaluated in each of these sub-regions. The location corresponding to the smallest cost function is the candidate of optimal solution. Depending on the spatial resolution requirements, systems and methods can be configured to pre-determine how many sub-regions need to be created or this can be a user-configurable parameter (e.g., in response to a user input). To improve efficiency, a coarser partition can be refined further to get finer resolution around the sub-region(s) identified in coarser resolution. That is, systems and methods disclosed herein can determine a coarse position corresponding to a volumetric region within the coordinate system, and then iterate until a desired resolution is achieved for the coordinates in space for the dipole location.

As another example, systems and methods disclosed herein can employ a Gauss-Newton method to solve the dipole model cost function, including the example formulations (e.g., least squares and log likelihood cost functions) disclosed herein.

For cost function written as summation of M components each is nonlinear with respect to unknown $$f(\vec{x}) = \frac{1}{2} \sum_{i=1}^{M} R_i^2(\vec{x}) \quad (14)$$

Where in dipole applications:

$$\vec{x} = [p^T, r^T]^T \quad (15)$$

Then Gauss-Newton numerical method for estimating the dipole location can be written as follows:

$$x_{k+1} = x_k - \lambda_k [J(x_k)^T J(x_k)]^{-1} J(x_k) R(x_k) \quad (16)$$

where J is the Jacobian matrix of the residue R with respect to x, and λ is the step size.

For the example of a dipole least square model function, such as in Eq. 2 above, the residue $R_i$ for measurement locations i on the patient's torso T can be expressed as a function of the moment p and location r as follows:

$$R_i(p, r) = \phi_T(r^i) - \frac{p \cdot (r - r^i)}{4\pi\sigma |r - r^i|^3} \quad (17)$$

As another example, the direct BEM least square model provided above from Eq. 12, the residue can be expressed as follows:

$$R_i(p, r) = \phi_T(r^i) - \frac{1}{4\pi} \oint_{\partial T} \phi_T(s) \frac{\partial\left(\frac{1}{r}\right)}{\partial n} \cdot ds - \frac{p \cdot (r - r^i)}{4\pi\sigma |r - r^i|^3} \quad (18)$$

In some examples, where the dipole is constantly localized (e.g., as part of a surgical or other procedure), assuming there is not much spatial difference between adjacent time instances, the initial location for computing dipole location can be set to the previous location, thereby providing a "warm start." For example, in the direct as well as other approaches, the search domain can be chosen in a neighborhood (e.g., within a predetermined spatial distance) around a previously computed dipole location. Similar to the iterative approaches, like gradient based approach or simplex search method, the last location can be used as the starting point to achieve similar computational efficiencies.

Figure 3:
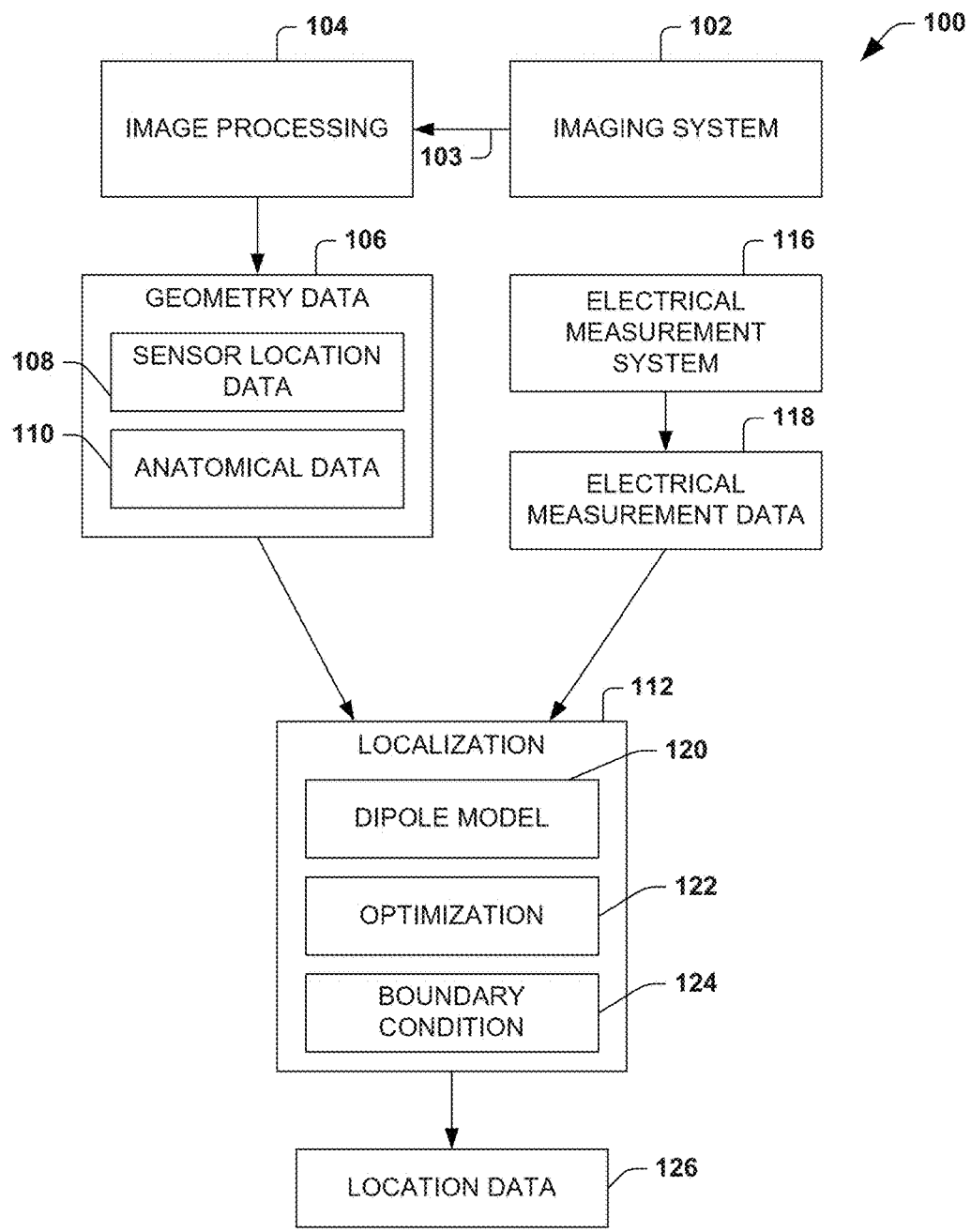
FIG. 3 depicts an example of a localization system.

FIG. 3 depicts an example of a system for localizing a source using a dipole model such as disclosed herein. The system 100 includes an imaging system 102 that generates an image data corresponding to a three-dimensional image space. For example, the engine system can employ one or more image modality (e.g., to provide three-dimensional image. Examples of imaging modalities include ultrasound, computed tomography (CT), 3D Rotational angiography (3DRA), fluoroscopy, magnetic resonance imaging (MRI), x-ray, positron emission tomography (PET), and the like. Such imaging can be performed separately (e.g., before or after the measurements) utilized to generate the electroanatomic data 14. Alternatively or additionally, some types of imaging may be performed concurrently with recording the electrical activity and localization methods disclosed herein.

An image processing system 104 can process the image acquired data from the imaging system (e.g., corresponding to one or more imaging modality) and provide geometry data 106. The image processing 104 can include segmentation of anatomical features from the digital image data 103, which can identify structural boundaries and fiducial markers within the image space. The geometry data 106 thus can include sensor location data 108 for each of the plurality of electrodes that are positioned on the volume of interest while the imaging system generates the imaging data 103. Thus, the location of each of the plurality of sensors (e.g., geometric centers or centroids of electrodes) can be determined in three-dimensional space by the imaging processing 104. Additionally, the image processing 104 can generate anatomical data 110 from the image data 103. The anatomical data 110 can correspond to segmented boundaries of one or more portions of the patient's body provided by the imaging data 103. This can include the exterior surface of the torso on which the sensors have been distributed during the imaging. The anatomical data further can include boundary of the heart, including one or more of epicardial or endocaridal surfaces.

The system 100 also includes an electrical measurement system 116 that is configured to receive signals from each of the sensors that are distributed down the patient's body at the locations represented by the sensor location data 108. The electrical measurement system 116 can include an arrangement of non-invasive sensors, invasive sensors positioned with the patient's body or a combination of non-invasive and invasive sensors at corresponding locations. In some examples, one or more invasive sensors can be movable within the patient's body, such as can be attached to a probe (e.g., a catheter). Such sensors on the probe can be positioned at a predetermined location relative to an electrode of other signal emitting element that is being localized by the system 100. The electrical measurement system 116 thus provides electrical measurement data 118 for discrete known locations based upon the sensed electrical signals by each of the sensors implemented by the system 116. Each electrical measurement in the data 118 can include time stamps, such as from a system clock. An applied localization signal can also be indexed to the same base to enable synchronization of the measurement data with the signal being localized. As mentioned, the signal can be applied by a signal generator or be natural biological signal.

Since the location of the probe is known relative to the signal emitting element being localized, the location of the probe or the device carrying the signal emitting element can be determined in the three-dimensional coordinate system defined by the geometry data 106. The relative dimensions and configuration of the probe within the coordinate system can also be readily determined to facilitate visualization in a corresponding output. Additionally, if more than one point is localized on such device, its orientation within the three-dimensional system space can also be determined. Given the dipole location, moment, and spacing between the poles, two points along the device can be determined. Multiple pairs of leads can be detected to allow a realistic rendering by polynomial interpolation (e.g., spline interpolation, such as cubic spline, B-spline or the like) or other rendering methods.

The system 100 includes a localization method 112 such as can correspond to the methods of FIG. 1 or 2 or as otherwise disclosed herein. The localization method 112 thus can correspond to instructions executable by one or more processing units within a computer. The localization method 112 thus employs a dipole model cost function 120. The dipole model is generated to represent the location and moment of a dipole as a function of measured electrical signals corresponding to the electrical measurement data 118.

The localization also includes an optimization function 122 that is configured to compute a solution for the dipole location and moment from the model 120, such as by implementing a cost function minimization or other optimization algorithm (e.g., least squares, Gaussian method, Gauss-Newton method) with respect to the model 120.

As disclosed herein, the localization 112 may be constrained by a boundary condition 124. The boundary condition 124 can be integrated into the dipole model cost function 120 to correspond to a direct approach for reconstructing electrograms and determining the location and moment of the dipole (e.g., as in Eq. 12). In other examples (e.g., corresponding to the method 50 of FIG. 2) the boundary condition can be implemented as preprocessing applied to the electrical measurement data 118 and geometry data 106 to improve the solution of the dipole model cost function.

Additionally or alternatively, in some examples, the localization 112 further can account for noise associated with the measurements, such as disclosed herein. By representing the measurement noise in the dipole model cost function 120, such as disclosed herein, improved accuracy in the computed dipole location can result. Other refinements of the cost function 120 and/or numerical method implemented by the optimization 122 can be used.

The localization method 112 generates the location data 126 to represent the location of the dipole within a given coordinate systems (e.g., based on the geometry data 106). The location data 126 thus can represent the computed dipole location as an absolute position in three dimensional space at one or more time instances as a function of the electrical measurement data 118 that has been synchronized with applied localization signal (e.g., aligning data by associated time stamps). By repeating the localization over time, the movement of the source (e.g., corresponding to a probe or other movable object) may be tracked over time, such as represented by a time sequence of the location data 126. In some examples, the location data 126 for each tracked probe can be averaged over time to provide a smooth and robust display of the probe's location. The averaging can also adopt other prior information such as the adjacent probe distance or the like. The location data 126 thus can be utilized to generate a visualization of the location, such as can be provided in a graphical map of the patient's anatomy.

Figure 4:
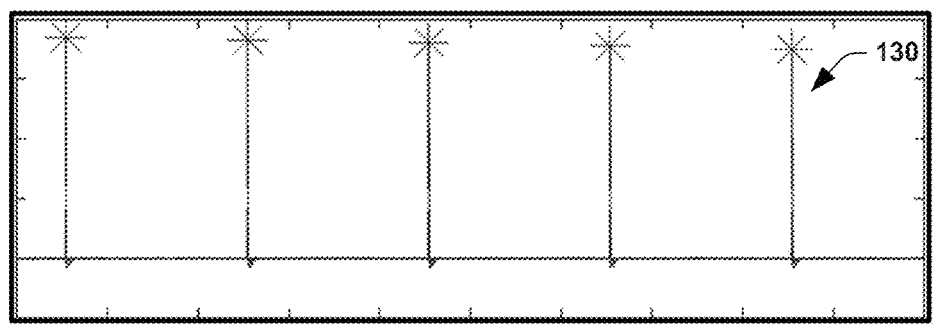
FIG. 4 depicts an example of a catheter signal generation.

FIG. 4 depicts an example of a localization signal 130 that includes a plurality of spikes over time. In the example of FIG. 4, each of the peaks of the spikes, peaks (designated by asterisks) correspond to the time that can be indexed and utilized for synchronizing the electrical signal measurements (e.g., by electrical measurement system 116 of FIG. 3) so that only the electrical measurement signals at the appropriate time index are utilized for the localization method being implemented (see, e.g., FIGS. 1-3).

Figure 5:
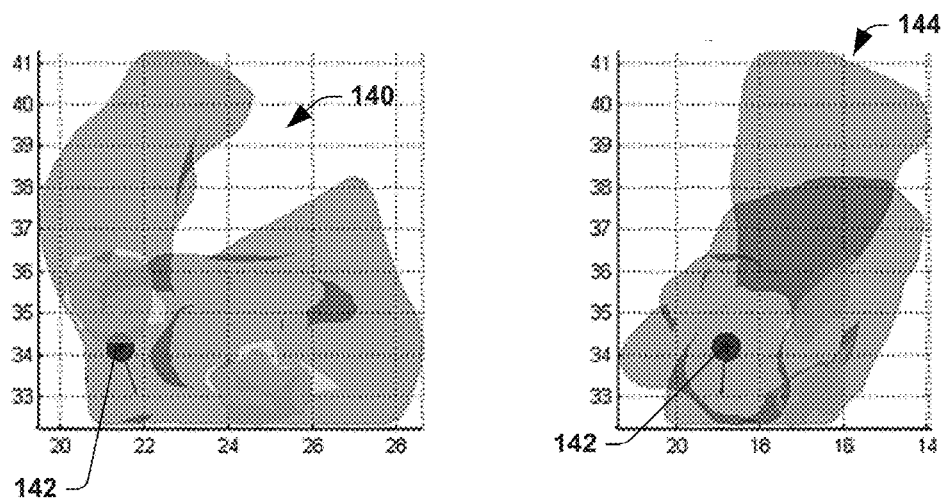
FIG. 5 depicts an example of a graphical map showing different views of graphical maps demonstrating localization results overlay.
Figure 5:
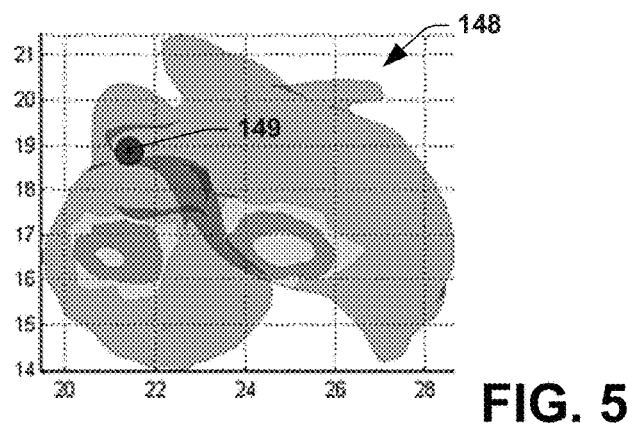

FIG. 5 depicts an example of a dipole location and moment overlaid on a graphical representation of a patient's heart. In FIG. 5, three graphical maps 140, 144, and 148 are shown for different views based on temporally and spatially consistent electrical measurement data and geometry data. For example, the map 140 demonstrates an anterior-posterior view of the right atrium. The location and moment of the dipole are demonstrated at 142. In the map 144, a right lateral view of the right atrium is demonstrated, and the location of the dipole is demonstrated at 146. Similarly, the graphical map 148 demonstrates the location of the dipole 149 and demonstrates a cranial view of the right atrium. In each of the maps 142, 144 and 146, the direction and magnitude of the dipole moment, extending outwardly from the center of the dipole location, can also be demonstrated.

Figure 6:
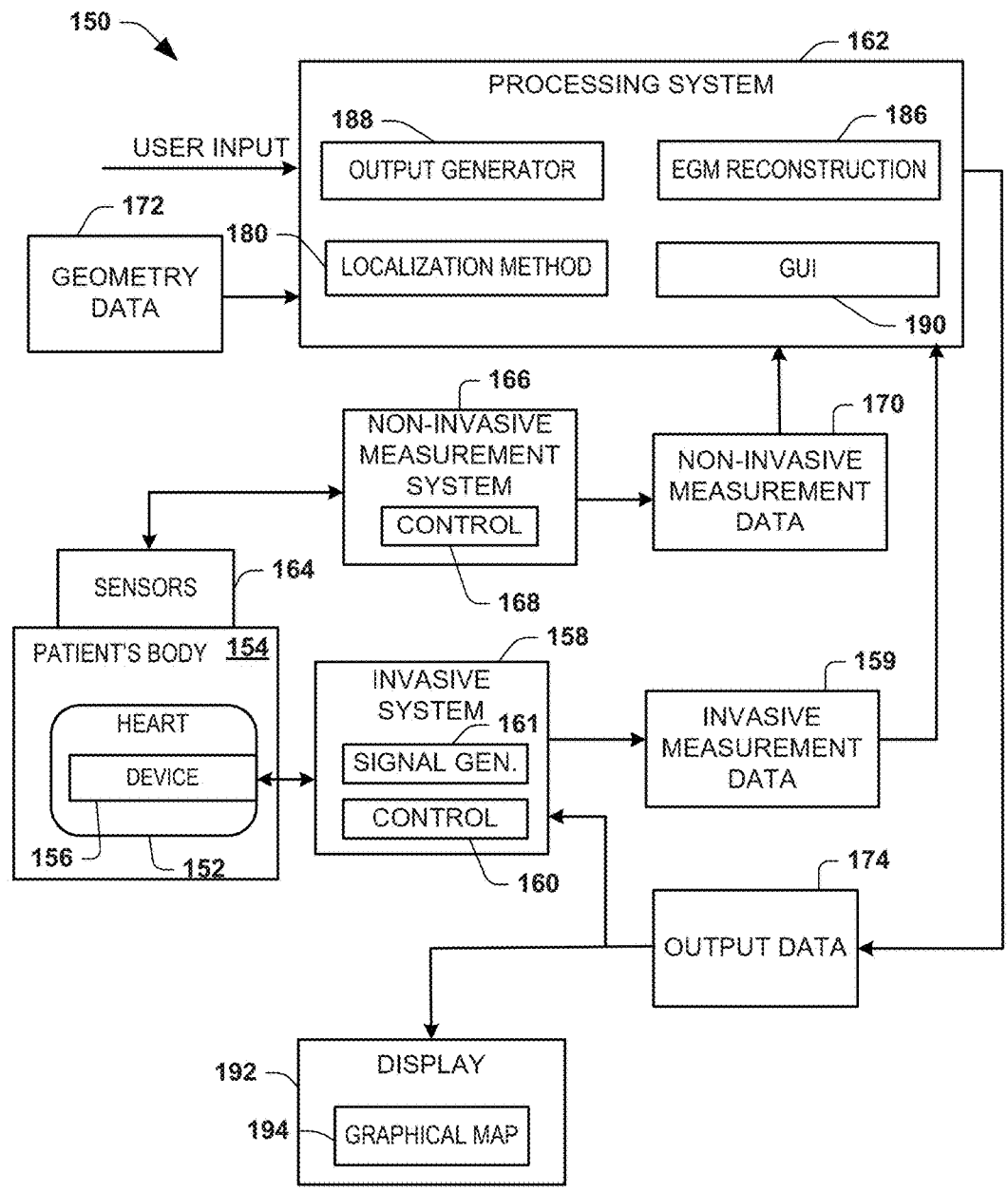
FIG. 6 depicts an example of a diagnostic/treatment system that can implement localization.

FIG. 6 depicts an example of a system 150 that can be utilized for localizing one or more sources of electrical signals within a volume of interest, such as a patient's body 154. The system 150 can be employed in conjunction with performing diagnostics and/or treatment of a patient. In some examples, the system 150 can be implemented to generate corresponding graphical outputs for signals and/or graphical maps for a patient's heart 152, including the position of a source, in real time as part of a procedure (e.g., monitoring of signals during an electrophysiology study). Additionally or alternatively, the system 150 can be utilized as part of a treatment procedure, such as to help guide a physician to deliver a therapy to a desired target site or region (e.g., containing identified arrhythmogenic electrical activity).

For example, an invasive device 156, such as a catheter, can be inserted into a patient's body 154. The device 156 includes one or more electrodes at configured to deliver energy that can be localized. The device 156 can apply the energy as a localization-specific signal, a pacing signal or to deliver another therapy, such as to electrically affect tissue (e.g., providing electrical therapy, or controlling delivery of chemical therapy, sound wave therapy, thermal therapy or any combination thereof).

The invasive system 158 can include a control 160 configured to control the signal generator 161 to apply the localization signal at one or more electrodes of the device 156. For example, the control 160 can control parameters (e.g., current, voltage, repetition rate, trigger delay, sensing trigger amplitude) of the signal generator 161 for delivering therapy (e.g., ablation or stimulation) via the electrode(s) to one or more location of the heart 152. The control 160 can set the therapy parameters and apply stimulation based on automatic, manual (e.g., user input) or a combination of automatic and manual (e.g., semiautomatic) controls. The invasive system 158 can also be configured to measure electrical activity via electrodes on the device 156, process the measured signals and provide corresponding invasive measurement data 159.

Additionally, the localization signals generated by signal generator 161 and applied to electrodes on the device 156 can be measured by a plurality of sensors 164 attached to the body 154 at locations known in a three-dimensional coordinate system. The sensors 164 thus can sense electrical activity, including signals corresponding to the applied localization signals. The sensors 164 can also sense other electrical signals, such as corresponding to real-time electrograms for the patient's heart.

The placement of the device 156 can be guided via a localization method 180, which can operate to localize the device 156 employing an equivalent dipole model and measurements, as disclosed herein. For example, the localization method 180 thus can compute a solution for a dipole model cost function to provide coordinates for the signal emitting element on the device to localize the device 156 and its electrodes, as disclosed herein. The guidance can be automated, semi-automated or be manually implemented based on information provided. During localization, the electrode on the device 156 can contact or not contact the patient's heart 152, endocardially or epicardially.

By way of further example, dipole localization can be implemented with respect to higher amplitude spikes or other signals that physician delivers for various clinical reasons. The localization engine would presumably be quite confident in this localization because SNR is high. Immediately following the clinical higher amplitude signal, a localization signal (e.g., normal low output pulses that do not stimulate or achieve the same therapeutic effect) can be delivered via one or more electrodes on the device 156, and the localization engine can then compute the position of the device in response to the localization signal. The difference in position for each of the different types localizations can be computed, and the difference can be used to calibrate the system. For example, if catheter delivers high amplitude pacing pulse for another reason at location A, dipole would localize to position A. Then with catheter remaining at location A' (the same or slightly displaced version of location A), the localization signal with lower output current can be applied, and localization engine can employ the dipole method to localizes to location A'. The system would calibrate position A' as true position A, and apply such computed calibration, which is stored in memory, for future localizations. The calibration can also be guided by intraprocedural imaging (e.g., x-ray fluoroscopy, ultrasound, CT or the like) to confirm the localized position matches the imaged position, which can be co-registered to a common coordinate system.

As a further example, the system 158 can be located external to the patient's body 154 and be configured to control therapy that is being delivered by the device 156. For instance, the system 158 can also control electrical signals provided via a conductive link electrically connected between the delivery device (e.g., one or more electrodes) 156 and the system 158. One or more sensors (not shown but could be part of the device) can also communicate sensor information back to the system 158.

The position of the device 156 in the heart 152 in three-dimensional space can be determined by performing localization as disclosed herein, which can be tracked intraoperatively via an output system 162 when implemented during a procedure. The location of the device 156 and the therapy parameters thus can be analyzed to help control therapy. Additionally, the application of therapy (e.g., manually in response to a user input or automatically provided) can cause a timestamp or other time identifier to be tagged (e.g., as metadata) to the measurement data to identify when the therapy is applied and trigger localization to identify the location where the therapy is applied via the device 156. Other metadata describing the therapy (e.g., type, delivery parameters etc.) can also be stored with the measurement data.

Figure 7:
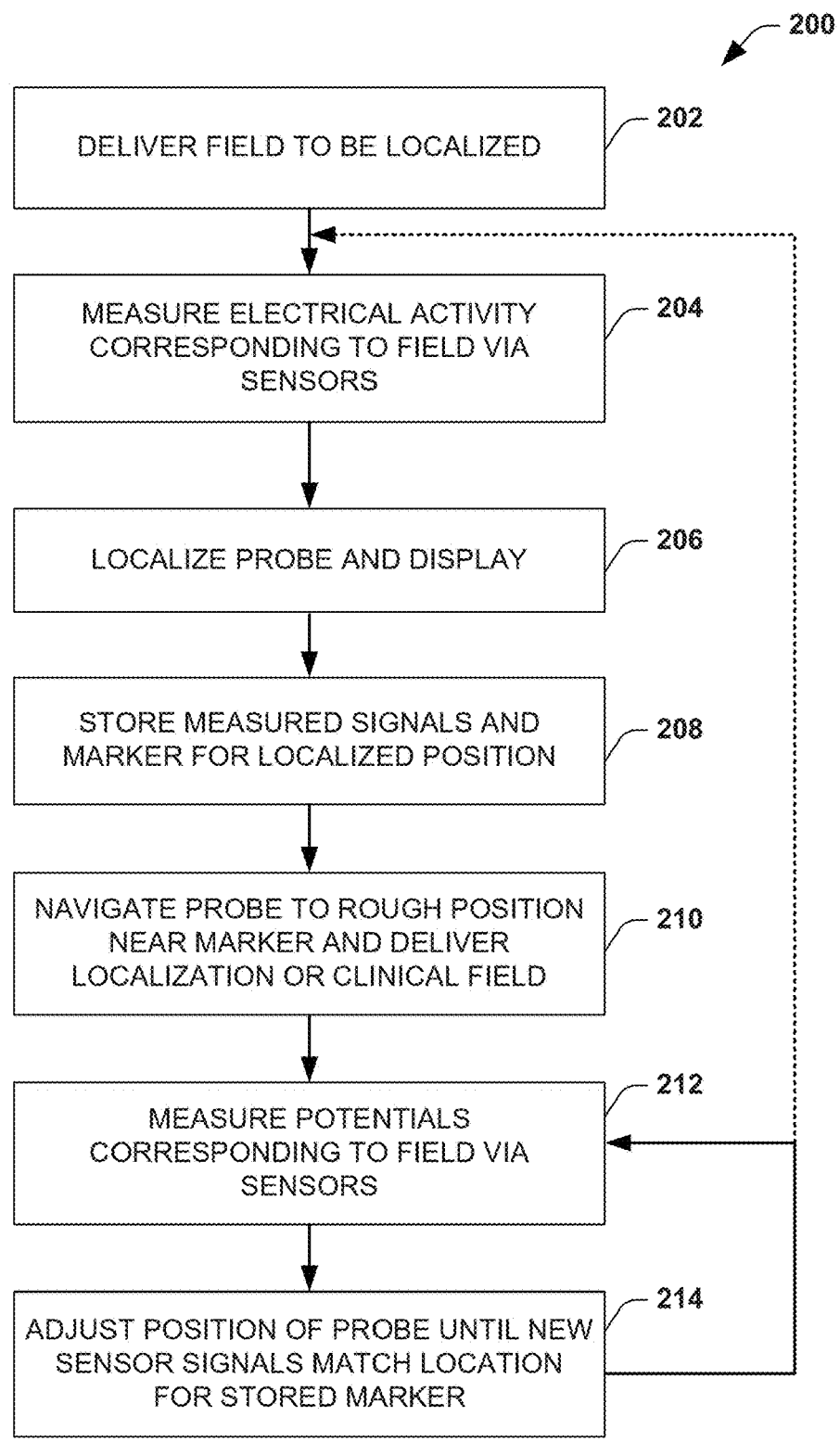
FIG. 7 is a flow diagram depicting an example of a method for using localization to navigate a probe.

Before, during and/or after delivering a therapy (e.g., via the system 158), one or more of the measurement system 158 or invasive system 166 can be utilized to acquire electrophysiology information for the patient. In the example of FIG. 7, one or more sensors 164 can be implemented as an array or other configuration for recording patient electrical activity. As one example, the sensors 164 can correspond to a high-density arrangement of body surface sensors that are distributed over a portion of the patient's torso for measuring electrical activity associated with the patient's heart (e.g., as part of an electrocardiographic mapping procedure). An example of a non-invasive sensor array that can be used is shown and described in International application No. PCT/US2009/063803, filed 10 Nov. 2009, which is incorporated herein by reference. Other arrangements and numbers of sensors 164 can be used. As an example, the sensors 164 can be a reduced set of sensors, which does not cover the patient's entire torso and is designed for measuring electrical activity for a particular purpose (e.g., an array of electrodes specially designed for analyzing AF and/or VF) and/or for monitoring a predetermined spatial region of the heart.

Sensors located on the device 156 can be utilized separately or in conjunction with the non-invasive sensors 164 for mapping electrical activity for an endocardial surface, such as the wall of a heart chamber, as well as for an epicardial surface. In each of such example approaches for acquiring real time patient electrical information, including invasively via the device 156, non-invasively via the sensors 164, or a combination of invasive and non-invasive sensing, the real time sensed electrical signals are provided to its corresponding measurement system 158, 166. Similar to the invasive system 158, the measurement system 166 can include appropriate controls and signal processing circuitry 168 for providing corresponding measurement data 170 that describes electrical activity detected by the sensors 164. The measurement data 170 can include analog and/or digital information (e.g., corresponding to electrogram data 14). Thus, the measurement data 159 and 170 can correspond to the measured electrical signals used for localization, as disclosed herein.

The control 168 can also be configured to control the data acquisition process (e.g., sample rate, line filtering) for measuring electrical activity and providing the measurement data 170. In some examples, the control 168 can control acquisition of measurement data 170 separately from the invasive system operation, such as in response to a user input. In other examples, the measurement data 170 can be acquired concurrently with and in synchronization with specific signals applied by the signal generator for purposes of localization. For instance, appropriate time stamps can be utilized for indexing the temporal relationship between the respective measurement data 159 and 170 and delivery of localization signals. The localization signals can be unique signals applied by the signal generator specifically to enable the localization. Additionally or alternatively, the signal generator can apply the localization signal, automatically or in response to a user input, for delivering a therapy. In either example, the non-invasive measurement system 166 can measure the body surface electrical activity via the sensor to provide corresponding measurement data 170. The processing system 162 thus can perform various signal processing and transformative methods, including a localization method 180 to localize the source according to the dipole localization method disclosed herein.

The localization method 180 can be configured to implement any of the variations of dipole localization methods based on the measurement data 170 and/or 159 and associated geometry data 172. The coordinates determined by the localization method 180 can be utilized by an output generator 188 provide the output data 174. The output data 174 can represent or characterize the position of the device in three-dimensional space based on coordinates of the dipole location determined according to the approach herein. Additionally, the location (or a corresponding path) can be displayed at the spatial locations across a cardiac envelope (e.g., on an epicardial or endocardial surface of the heart 152). The output generator 188 can display the location separately. In other examples, the location can be combined with other output data, such as to display location information on graphical map of electrical activity of the heart 152.

Since, in some examples, the measurement system 166 can measure electrical activity of a predetermined region or the entire heart concurrently (e.g., where the sensors 164 covers the entire thorax of the patient's body 154), the measurements are spatially and temporally consistent. Consequently, the accuracy in the resulting output location provided in the output data 174 can be increased when compared to other localization techniques, such as to supply the user with a more accurate and global information to facilitate monitoring and application of therapy. Additionally or alternatively, the localization can be continuous process and/or be synchronized with respect to the application of therapy provided by the system 158.

By way of further example, the electrical measurement data is obtained non-invasively via body surface sensors 164, electrogram reconstruction 186 can be programmed to compute an inverse solution and provide corresponding reconstructed electrograms based on the measurement data 170 and the geometry data 172. The reconstructed electrograms thus can correspond to electrocardiographic activity across an envelope, and can include static (three-dimensional at a given instant in time) and/or be dynamic (e.g., four-dimensional map that varies over time). Examples of inverse algorithms that can be utilized in the system 150 include those disclosed in U.S. Pat. Nos. 7,983,743 and 6,772,004, which are incorporated herein by reference. The EGM reconstruction 186 thus can reconstruct the body surface electrical activity measured via the sensors 164 onto a multitude of locations on an envelope (e.g., greater than 1000 locations, such as about 2000 locations or more). In other examples, the output system 162 can compute electrical activity over a sub-region of the heart based on electrical activity measured invasively, such as via the device 156 (e.g., including a basket catheter or other form of measurement probe). As mentioned above, in some examples, the localization method 180 can employ the electrogram reconstruction 186 to impose a boundary condition on the dipole model cost function (see, e.g., FIG. 2). Additionally or alternatively, the dipole model cost function implemented by localization method 180 can directly parameterize the boundary condition (e.g., as in Eq. 12).

As disclosed herein, an envelope (e.g., cardiac envelope) can correspond to a three-dimensional surface geometry corresponding to a patient's heart, which surface can be epicardial or endocardial. Alternatively or additionally, the envelope can correspond to a geometric surface that resides between the epicardial surface of a patient's heart and the surface of the patient's body where the sensors 164 have been positioned. Additionally, the geometry data 172 that is utilized by the electrogram reconstruction 186 can correspond to actual patient anatomical geometry, a prepogrammed generic model or a combination thereof (e.g., a model that is modified based on patient anatomy). The location computed via the single equivalent dipole model can be co-registered with the geometry.

As an example, the geometry data 172 may be in the form of graphical representation of the patient's torso, such as image data acquired for the patient. Such image processing (e.g., imaging processing 104) can include extraction and segmentation of anatomical features, including one or more organs and other structures, from a digital image set. Additionally, a location for each of the sensors 164 can be included in the geometry data 172, such as by acquiring the image while the electrodes are disposed on the patient and identifying the electrode locations in a coordinate system through appropriate extraction and segmentation. Other non-imaging based techniques can also be utilized to obtain the position of the electrodes in the sensor array in the coordinate system, such as a digitizer or manual measurements, which can be stored in the geometry data 172.

The geometry data 172 can correspond to a mathematical model, such as can be a generic model or a model that has been constructed based on image data for the patient. Appropriate anatomical or other landmarks, including locations for the sensors 164 can be identified in the geometry data 172 for display in conjunction with computed location information for the device. The identification of such landmarks and can be done manually (e.g., by a person via image editing software) or automatically (e.g., via image processing techniques).

By way of further example, the geometry data 172 can be acquired using nearly any imaging modality based on which a corresponding representation of the geometrical surface can be constructed, such as described herein. Such imaging may be performed concurrently with recording the electrical activity that is utilized to generate the patient measurement data 170 or the imaging can be performed separately (e.g., before or after the measurement data has been acquired).

The output generator 188 can generate corresponding output data 174 that can in turn be provide a corresponding graphical output in a display 192, such as including an indication of location for the device 156. The location can be displayed on graphical model of patient anatomy or superimposed on the electrocardiographic map 194. The location can take other forms to provide guidance to the user, such as disclosed herein.

A graphical user interface (GUI) 190 can be employed to interact with the processing system 162 and/or the systems 158 and/or 166. For example, the GUI can be used to set parameters associated with the displayed graphical representation, corresponding to an output visualization of the computed map, such as including selecting a time interval, a type of information that is to be presented in the visualization and the like can be selected in response to a user input. Additionally, a user can employ the GUI 190 to selectively program one or more parameters (e.g., desired resolution, convergence thresholds, model and spatial thresholds, filter parameters and the like) and or select dipole model cost function and associated optimization functions utilized by the localization method 182.

Additionally, in some examples, the output data 174 can be utilized by the invasive system 158 in connection with controlling delivery of therapy or monitoring electrical characteristics. The control 160 that is implemented can be fully automated control, semi-automated control (partially automated and responsive to a user input) or manual control based on the output data 174. In some examples, the control 160 of the invasive system 158 can utilize the output data 174 to control one or more therapy parameters. As an example, the control 160 can control delivery of pacing therapy to a site of the heart (e.g., epicardial or endocardial wall) based on one or more arrhythmia drivers identified. In other examples, an individual can view the map 194 generated in the display to manually control the therapy system at a location determined based on this disclosure. Other types of therapy and devices can also be controlled based on the output data 174 and corresponding graphical map 194.

FIG. 7 depicts an example of a method 200 for navigating a device using dipole localization. The method 200, for example can be implemented in the system 150 of FIG. 6, for example. Accordingly, reference can be made to FIG. 6 for supplemental information pertaining to certain features of the method 200. At 202, an applied electrical field is delivered at a source that is to be localized. The electric field can correspond to a specially designed localization field or a field that is applied for a clinical application (e.g., pacing or the like, such as provided by the signal generator 161 to an electrode on the device 156).

At 204, the method 200 includes measuring potentials corresponding to the applied field via the sensors. Sensors (e.g., sensors in array 154 or on the device 156). At 206, the device carrying the field delivery element (e.g., providing the electric field at 202) is localized (e.g., optimization of dipole model cost function) and displayed on a corresponding output device. The localization at 206 can be implemented according to the approaches disclosed herein (e.g., methods 10 or 50, localization method 112, localization method 180). The localized position thus can correspond to an absolute position in three dimensional space (e.g., a volumetric space defined by a coordinate system registered to the patient's body) that can be attributed to a probe or other device that is being moved within the patient's body such as to a target location. The display thus can provide a visual representation to help guide the user for adjusting the position of the probe to a desired target.

At 208, measured signals and graphical marker for each localized position determined at 206 can be stored in memory. For example, the markers stored at 208 can be defined as some fiducial marker, such as an anatomical landmark identified from geometry segmented via imaging, such as CT, MRI or other imaging modality disclosed herein. As another example, the stored position information can be used to graphically construct a trail to identify a previous location or path of travel as the probe or other devices advance from one location to another, such as a target site for delivery of therapy.

At 210, the probe can be navigated to a rough position near the marker and deliver a localization electric field. As an example, the marker can be determined using other calculations based upon measuring electrical signals emitting from the patient's heart such as to identify focal points or other locations associated with a point of region identified as including arrhythmogenic activity for which therapy is desired.

At 212, as part of the navigation process potential corresponding to the field emitting from the device are measured (as at 204). At 214, the position f the probe can be adjusted until the localized position of the probe matches the location of the stored marker at 210. Thus the process can repeat between 212 and 214 until the difference between the localized position and the marker match within desired amount. The process can be repeated for any number of target locations that can be identified and marked on the graphical map. Additionally from 214, the method can return to 204 to repeat 204-214 over time during which the method 200 is being performed.

As yet another example the location information can be utilized in conjunction with anatomic geometry data (e.g., data 106 or 172 acquired via an imaging modality) to navigate within this geometry. Such location information can also be utilized to determine wall thickness of the heart wall at one or more determined locations. For instance, before localizing the signal emitting probe (e.g., catheter), an imaging modality, such as a CT scan or MRI can be used CT scan to segment (localize) epicardial shell with respect to a non-invasive sensor array. Since the position of the epicardial shell is known with respect to the sensor array, then, when the signal emitting probe (e.g., catheter) is inside heart, a user can rove catheter around within one or more chambers to generate the endocardial geometry.

For example, the physician moves catheter around, until it has covered the entire endocardial surface area of one or more chambers. As catheter moves, localizing electrical pulses can be generated at a sufficiently high periodic rate (e.g., a default or user-programmable rate) to enable a dipole localization method (e.g., as shown in FIG. 1 or 2, or via method 180 of FIG. 7) to continuously localize the tip of the catheter and thereby construct an endocardial shell in a three-dimensional coordinate system—also with respect to the non-invasive sensors locations. Thus, at this stage the endocardial shell and the epicardial shell are both known in a common coordinate system, and the corresponding location information can be stored in memory. With these two pieces of information, the system can compute wall thickness at any location as the difference between the nearest location on the epicardial shell and the nearest location on the endocardial shell.

The resulting three-dimensional geometry for the endocardial that is determined further can be stored in memory as a volumetric region of interest, which can be used for further mapping and navigation of the signal emitting object (e.g., catheter or other probe). For example, one or more sites (e.g., stored in memory as 3D positions) residing on or within such volumetric region of interest can be identified as destination sites to which the signal emitting object (e.g., catheter or other probe) can be moved based monitoring the current location of the object computed based on substantially real time sensor measurements, as disclosed herein.

Additionally, the systems and methods disclosed herein can be employed to re-navigate to a stored position. For example, stored sensor measurements, corresponding to a dipole field at a given target location, can be stored in memory. A user can navigate a signal-emitting object back to the given target location by matching a new computed location (determined from substantially real time sensor measurements) to the stored dipole location representing the given target location. The matching can be computed based on computing a difference between stored dipole location data and the new computed locations based on current sensor measurements.

Additionally, one or more resulting indicators (e.g., visual and/or audible indicators) can be generated based on the computed difference to provide guidance to assist the user to move the signal emitting object to the desired target location. The indicator can be generated for the ultimate destination and/or for a predetermined path of travel from a current location to the target destination, which can be stored in memory. The path of travel can be a stored path of travel that has already been traversed (e.g., during a previous procedure). Additionally or alternatively, the path of travel can be predicted path of travel from a current computed location of the signal emitting object to the target destination. The target destination can be single point of interest or it can be volumetric region of interest.

As part of the workflow, the coordinates in space determined for the unknown location can be stored in memory over a plurality of time instances that collectively define a three-dimensional path of travel. An output trace corresponding to the path of travel can be displayed with respect to patient anatomy that is co-registered with the coordinates in space. This, in effect, can be used to observe a path of the catheter or other object being moved within the patient's anatomy, which can include blood vessels (e.g. arteries and veins) as well as the patient's heart or other anatomic region of interest. The display of the path can be animated over time, such as to demonstrate movement velocity (speed and trajectory) of the catheter over time. In other examples, the trace can be presented to demonstrate the path such as to facilitate re-tracing the path by an object (e.g., manually, automatically and/or robotically).

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A method comprising:
    storing measurement data in memory representing measured electrical signals at each of a plurality of known measurement locations in a given coordinate system in response to an applied signal at an unknown location in the patient's body and in the given coordinate system the applied signal comprising a predetermined waveform that is distinct from anatomically generated signals, the plurality of known measurement locations comprising locations of respective electrophysiological sensors in the given coordinate system registered with respect to a patient's anatomy and used to sense the measured electrical signals, and the locations of the respective sensors comprising at least one of non-invasive locations distributed about a surface of the patient's body or invasive locations within the patient's body where the sensors have been attached;
    providing, to a processor communicatively coupled to the memory, a dipole model cost function having parameters representing a dipole location and moment corresponding to the applied signal;
    imposing a boundary condition on the dipole model cost function; and
    determining, with the processor, the unknown location in the given coordinate system, corresponding to the dipole location, based on the stored measurement data and the dipole model cost function with the boundary condition imposed thereon.

2. The method of claim 1, wherein imposing the boundary condition further comprises:
    reconstructing the measured electrical signals on a spatial envelope in the given coordinate system and storing the reconstructed electrical signals in the memory, the unknown location in the given coordinate system being determined based on the dipole model cost function and the reconstructed electrical signals.

3. The method of claim 2, wherein the spatial envelope is a first spatial envelope, and wherein determining the unknown location further comprises:
    repeatedly reconstructing electrical signals to another envelope at a location between the first spatial envelope and the unknown location and determining the unknown location based on applying the reconstructed electrical signals on the other envelope to the dipole model cost function until a difference between the dipole location and a previously determined dipole location is less than a threshold.

4. The method of claim 1, wherein the boundary condition is integrated in the dipole model cost function.

5. The method of claim 1, wherein the dipole model cost function is configured to parameterize noise associated with the measured electrical signals.

6. The method of claim 5, wherein the noise is parameterized in the dipole model cost function as a variance associated with the measured electrical signals.

7. The method of claim 6, wherein the variance associated with the measured electrical signals varies depending on the known measurement locations for at least some of the measured electrical signals.

8. The method of claim 1, further comprising computing a difference between each of the measured electrical signals with respect to a reference electrical signal at a predefined location, and wherein the dipole model cost function parameterizes an electric field of the applied signal with respect to the computed difference.

9. The method of claim 8, wherein the predefined location is selected from one of the plurality of known measurement locations.

10. The method of claim 9, wherein the predefined location is chosen regionally for each of the measured electrical signals according to the known measurement locations of the measured electrical signals to help compensate for effects of inhomogeneity through a volume in which the applied signal is provided.

11. The method of claim 1, wherein determining the unknown location in the given coordinate system further comprises minimizing a difference based on the measured electrical signals and a dipole field computed for the dipole model cost function over a set of locations residing in the given coordinate system, the unknown location in the given coordinate system being determined based on the minimizing.

12. The method of claim 1, wherein determining the unknown location in the given coordinate system further comprises implementing a Gauss-Newton method to determine the unknown location in the given coordinate system.

13. The method of claim 1, further comprising:
storing in memory the determined unknown location over a plurality of time instances that collectively define a three-dimensional path of travel; and
displaying an animated output trace corresponding to the path of travel with respect to patient anatomy that is co-registered with the coordinates in space.

14. The method of claim 1, further comprising displaying an indication of the determined unknown location in a graphical map that includes anatomical geometry.

15. The method of claim 1, wherein the applied signal comprises a predetermined waveform that is applied from electrode disposed on a probe.

16. A method comprising:
storing measurement data in memory representing measured electrical signals at each of a plurality of known locations in a given coordinate system in response to an applied signal at an unknown location in the patient's body and residing in the given coordinate system, the applied signal comprising a predetermined waveform that is distinct from anatomically generated signals, the plurality of known measurement locations comprising locations of respective electrophysiological sensors in the given coordinate system registered with respect to a patient's anatomy and used to sense the measured electrical signals, and the locations of the respective sensors comprising at least one of non-invasive locations distributed about a surface of the patient's body or invasive locations within the patient's body where the sensors have been attached;
providing, to a processor communicatively coupled to the memory, a dipole model cost function having unknown parameters representing a dipole location and moment as a function of the measured electrical signals, the dipole model cost function also parameterizing noise associated with the measured electrical signals; and
determining, with the processor, the unknown location in the given coordinate system, corresponding to the dipole location, based on the dipole model and the stored measurement data.

17. The method of claim 16, wherein the noise is parameterized in the dipole model cost function as a variance representing noise associated with the measured electrical signals at each of the plurality of known locations.

18. The method of claim 17, wherein the variance associated with the measured electrical signals has a value that varies depending on the known locations for at least some of the measured electrical signals.

19. The method of claim 16, further comprising computing a difference between each of the measured electrical signals with respect to a reference electrical signal at a predefined location, and wherein the dipole model cost function parameterizes an electric field of the applied signal with respect to the computed difference.

20. The method of claim 19, wherein the predefined reference location is selected either from one of the plurality of known locations or is chosen regionally for each of the measured electrical signals according to the known locations of the measured electrical signals to help compensate for effects of inhomogeneity through a volume in which the applied signal is provided.

21. The method of claim 16, further comprising imposing a boundary condition on the dipole model cost function, wherein the unknown location in the given coordinate system is determined with the boundary condition imposed thereon.

22. The method of claim 21, wherein imposing the boundary condition further comprises:
reconstructing the measured electrical signals on a spatial envelope in the given coordinate system and storing the reconstructed electrical signals in the memory, the unknown location in the given coordinate system being determined based on the dipole model cost function and the reconstructed electrical signals.

23. The method of claim 21, wherein the imposed boundary condition is integrated in the dipole model cost function.

24. A system comprising:
non-transitory memory that stores geometry representing a plurality of measurement locations around a volume and anatomical data registered in a given coordinate system with respect to a patient's anatomy;
a measurement system that receives signals measured at the plurality of measurement locations, including in response to a signal applied to a location in the patient's body and within the volume, and provides measurement data representing the measured signals at each of the plurality of measurement locations, the measurement data being stored in the memory, the applied signal comprising a predetermined waveform that is distinct from anatomically generated signals, the plurality of measurement locations comprising locations of respective electrophysiological sensors in the given coordinate system used to sense the measured signals, and the locations of the respective sensors comprising at least one of non-invasive locations distributed about a surface of the patient's body or invasive locations within the patient's body where the sensors have been attached;
a computer-processor-implemented localization system that includes a dipole model cost function having unknown parameters representing a dipole location and moment, corresponding to the applied signal, the localization system imposing a boundary condition on the dipole model cost function to determine the location of the applied signal in the given coordinate system, corresponding to the dipole location, based on the measurement data.

25. The system of claim 24, wherein the localization system imposes the boundary condition on the dipole model cost function by reconstructing the measured signals on a spatial envelope in the given coordinate system and storing the reconstructed electrical signals in the memory, the location of the applied signal in the given coordinate system being determined based on the dipole model cost function and the reconstructed electrical signals.

26. The system of claim 24, wherein the boundary condition is integrated in the dipole model cost function used to determine the location of the applied signal.

27. The system of claim 24, wherein the dipole model cost function is further configured to parameterize noise associated with the signals measured at the plurality of measurement locations.

28. The system of claim 24, further comprising:
a signal generator that generates the applied signal; and an output generator that generates output data, which is stored in the memory, for displaying an indication of the location with respect to an anatomical map.

* * * * *